(12) United States Patent
Geppert et al.

(10) Patent No.: US 11,617,874 B2
(45) Date of Patent: Apr. 4, 2023

(54) LUER CONNECTOR

(71) Applicant: NORDSON CORPORATION, Westlake, OH (US)

(72) Inventors: Kevin C. Geppert, Eagan, MN (US); Alexander Cromett, St. Paul, MN (US)

(73) Assignee: Nordson Corporation, Westlake, OH (US)

( * ) Notice: Subject to any disclaimer, the term of this patent is extended or adjusted under 35 U.S.C. 154(b) by 319 days.

(21) Appl. No.: 16/315,734

(22) PCT Filed: Jul. 6, 2017

(86) PCT No.: PCT/US2017/040914
§ 371 (c)(1),
(2) Date: Jan. 7, 2019

(87) PCT Pub. No.: WO2018/009674
PCT Pub. Date: Jan. 11, 2018

(65) Prior Publication Data
US 2020/0179671 A1    Jun. 11, 2020

Related U.S. Application Data

(60) Provisional application No. 62/359,709, filed on Jul. 8, 2016.

(51) Int. Cl.
*A61M 39/10* (2006.01)

(52) U.S. Cl.
CPC ...... *A61M 39/1011* (2013.01); *A61M 39/105* (2013.01); *A61M 2039/1027* (2013.01);
(Continued)

(58) Field of Classification Search
CPC ............ A61M 39/1011; A61M 39/105; A61M 2039/1027; A61M 2039/1033;
(Continued)

(56) References Cited

U.S. PATENT DOCUMENTS

| 4,616,859 A | 10/1986 | Brunet |
| 5,123,677 A | 7/1992 | Kreczko et al. |

(Continued)

FOREIGN PATENT DOCUMENTS

| EP | 0459812 A1 | 12/1991 |

OTHER PUBLICATIONS

ISA/220—Notification of Transmittal of Search Report and Written Opinion of the ISA, or the Declaration dated Oct. 27, 2017 for WO Application No. PCT/US17/040914.

(Continued)

*Primary Examiner* — Shefali D Patel
(74) *Attorney, Agent, or Firm* — BakerHostetler

(57) ABSTRACT

A slip luer assembly includes a hub member and a latch member coupled to the hub member. The hub member includes an outer hub surface, an inner hub surface and a window surface. The window surface defines a window extending from the outer hub surface to the inner hub surface. The latch member includes at least one blade. The latch member is configured to be actuated between a first position and a second position. In the first position, the at least one blade is not positioned within the window of the hub member. In the second position, the at least one blade is positioned at least partially within the window of the hub member.

14 Claims, 9 Drawing Sheets

(52) U.S. Cl.
CPC ............... *A61M 2039/1033* (2013.01); *A61M 2039/1066* (2013.01); *A61M 2039/1077* (2013.01); *A61M 2039/1083* (2013.01)

(58) Field of Classification Search
CPC .. A61M 2039/1066; A61M 2039/1077; A61M 2039/1083; A61M 39/1055
See application file for complete search history.

(56) References Cited

U.S. PATENT DOCUMENTS

| | | | |
|---|---|---|---|
| 5,496,274 A * | 3/1996 | Graves | ............... A61M 39/1011 604/192 |
| 2006/0103134 A1 | 5/2006 | Kerin | |
| 2007/0132235 A1 | 6/2007 | Catlow | |
| 2013/0147188 A1 * | 6/2013 | Christian, Jr. | .......... F16L 21/08 285/320 |

OTHER PUBLICATIONS

IPEA/409—International Preliminary Report on Patentability dated Jan. 17, 2019 for WO Application No. PCT/US17/040914.

* cited by examiner

LUER CONNECTOR

CROSS REFERENCE TO RELATED APPLICATIONS

This application is a National Stage of International Patent App. No. PCT/US2017/040914, filed Jul. 6, 2017, which claims priority to U.S. Provisional Patent Application No. 62/359,709, filed Jul. 8, 2016, the disclosures of which are incorporated by reference herein in their entirety.

TECHNICAL FIELD

This disclosure relates generally to a connector fitting, and more particularly, to a slip luer connector assembly and a method of using the slip luer connector assembly for connecting and disconnecting syringes.

BACKGROUND

Luer connectors are used for attaching syringes, catheters, hubbed needles, intravenous tubes, or other interlocking tubes together. Current luer connectors have been known to cause problems during use by disconnecting or leaking under strong force or bending. In some applications, such as surgical procedures, the connection between the interlocking tubes needs to resist side loads, bending, and/or internal pressure present during use of the slip luer connector. A solution to overcome these issues includes the use of luer threads, which secure the male and female tubes together. However, although luer threads may provide a more secure connection, they also increase the amount of time required to switch between interlocking tubes and require more force to tighten and loosen tubes.

Thus, an improved and/or simplified slip luer connector for connecting interlocking tubes is desired to increase the effectiveness of the connection while minimizing leakage between the tubes and minimizing delay time when switching tubes.

SUMMARY

An aspect of the present disclosure provides a luer assembly. The luer assembly comprises a hub member and a latch member. The hub member has a hub receiving portion that includes an outer hub surface, an inner hub surface, and a window surface. The inner hub surface defines a channel that extends at least partially through the hub member. The window surface defines a window that extends from the outer hub surface to the inner hub surface. The latch member is coupled to the hub member and includes at least one blade. The latch member is configured to be actuated between a first position and a second position. In the first position, the at least one blade is not positioned within the window of the hub member, and in the second position, the at least one blade is positioned at least partially within the window of the hub member.

Another aspect of the present disclosure provides a method for operating a luer assembly. The luer assembly includes a latch member and a hub member. The method comprises inserting a male slip luer into the hub member; and actuating the latch member from a first position to a second position. The hub member includes an outer hub surface, an inner hub surface that defines a luer channel that extends at least partially through the hub member, and a window surface that defines a window that extends from the outer hub surface to the inner hub surface. The male slip luer is inserted into the luer channel. The latch member includes at least one blade. In the first position of the latch member, the at least one blade is not positioned within the window of the hub member, in the second position of the latch member, the at least one blade is positioned at least partially within the window of the hub member.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION

Figure 1:
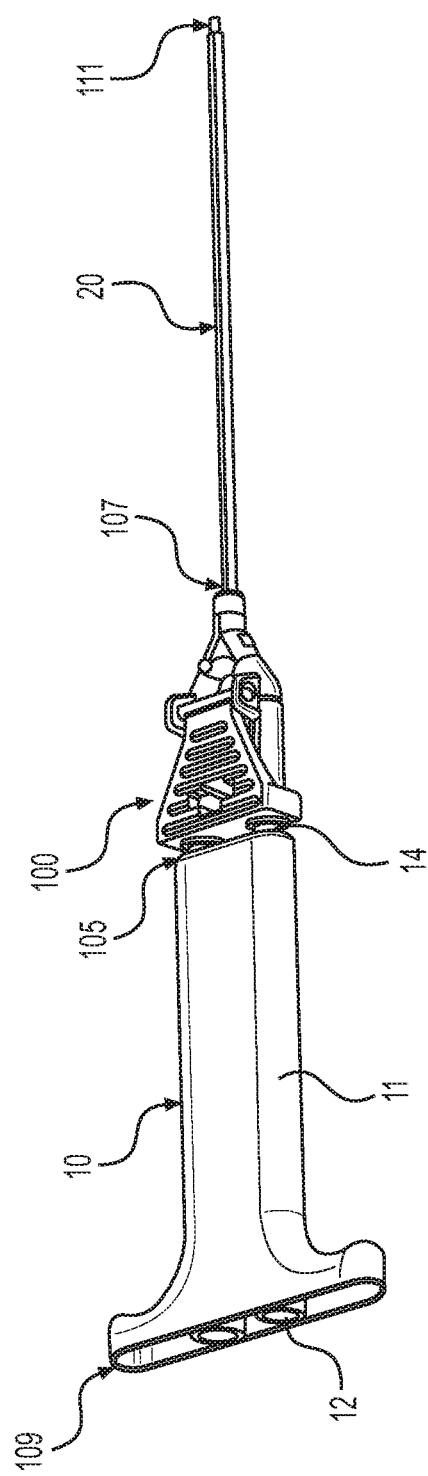
FIG. 1 illustrates a perspective view of a syringe, a luer assembly, and a tube interconnected, according to an aspect of this disclosure.

This disclosure relates generally to a luer connector configured to connect a syringe to a tube. The luer connector may receive and lock a portion of the syringe, minimizing the likelihood that the syringe will disconnect during use. The luer connector includes a hub member and a latch member coupled to the hub member. The hub member defines at least one female luer connector having at least one window extending from an inner surface to an outer surface. The female luer connector is configured to receive a male luer connector of the syringe. The latch includes at least one blade. When the male luer connector of the syringe is positioned within the female luer connector of the hub member, the latch may be moved relative to the hub member to position the at least one blade within the at least one window of the hub member to engage the male luer connector. The engagement between the male luer connector and the latch member locks the syringe within the luer connector.

Certain terminology is used in the description for convenience only and is not limiting. The words "proximal" and "distal" refer to positions or directions toward and away from, respectively, an individual operating a syringe 10. The words "longitudinal," "radial," and "transverse" designate directions in the drawings to which reference is made. The term "substantially" is intended to mean considerable in extent or largely but not necessarily wholly that which is specified. The terminology includes the above-listed words, derivatives thereof and words of similar import.

Figure 2:
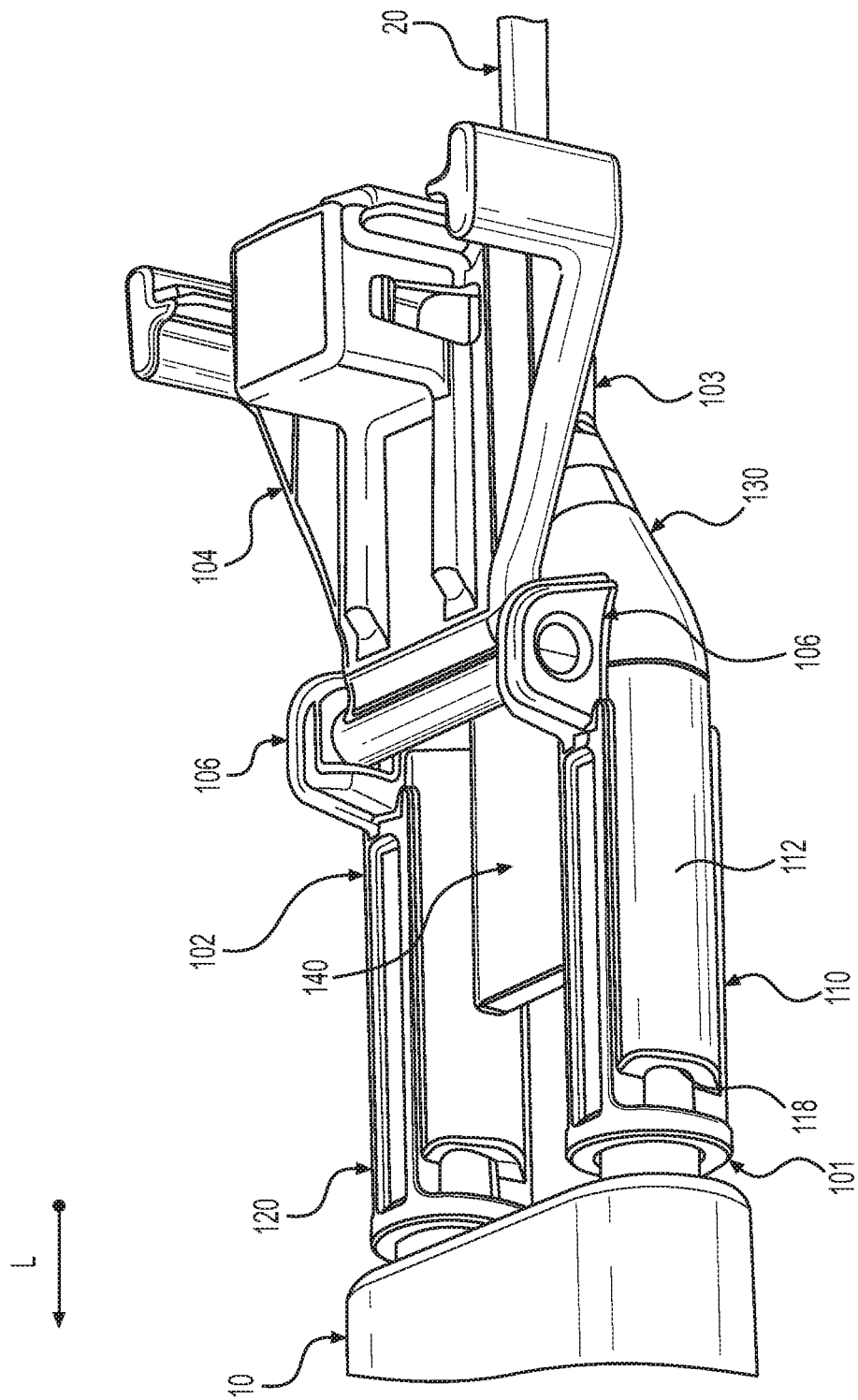
FIG. 2 illustrates a perspective view of a luer assembly in an open position with a syringe and a tube attached thereto, according to an aspect of this disclosure.
Figure 3:
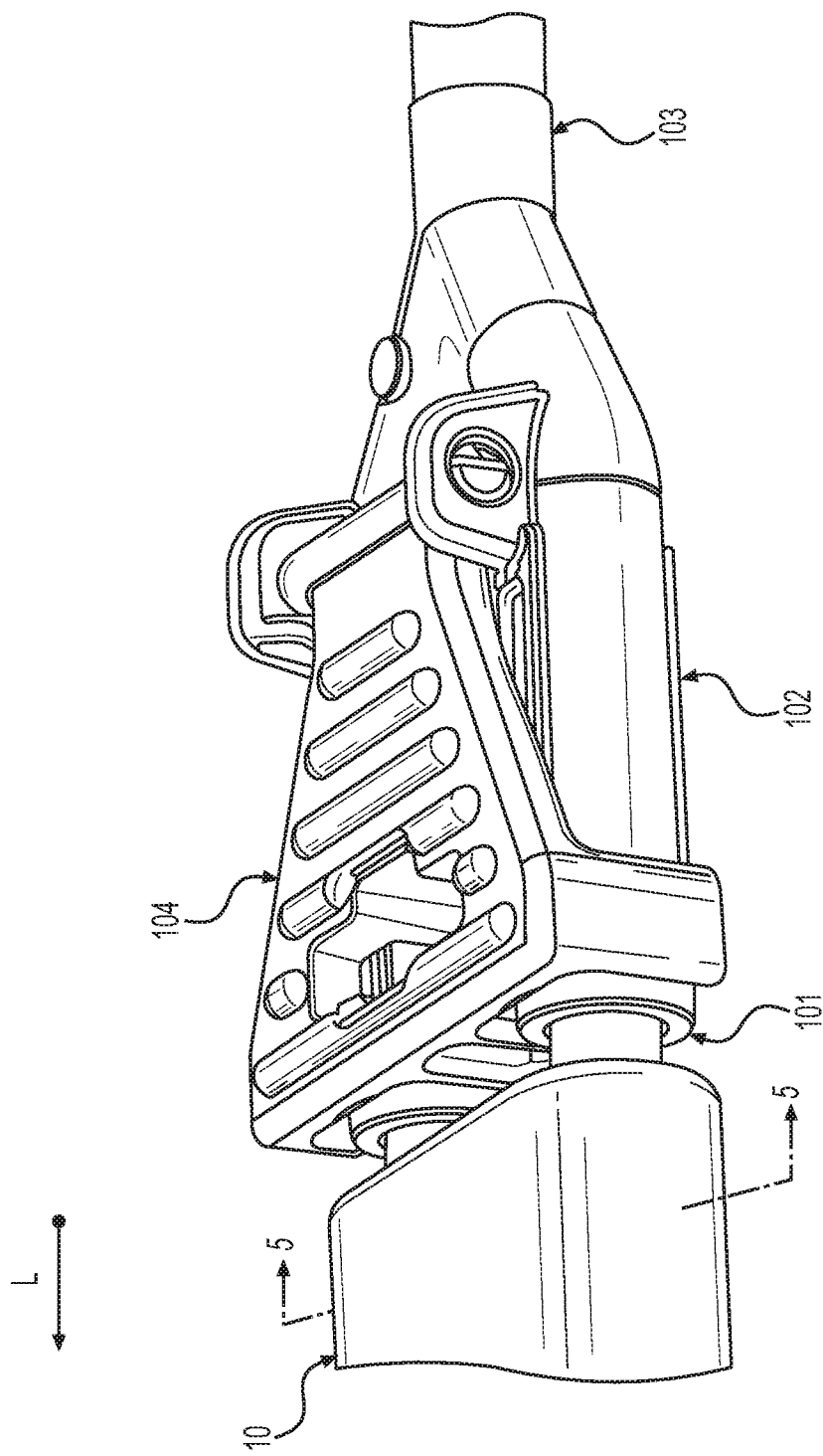
FIG. 3 illustrates a perspective view of a luer assembly in a closed position with a syringe and a tube attached thereto, according to an aspect of this disclosure.
Figure 4:
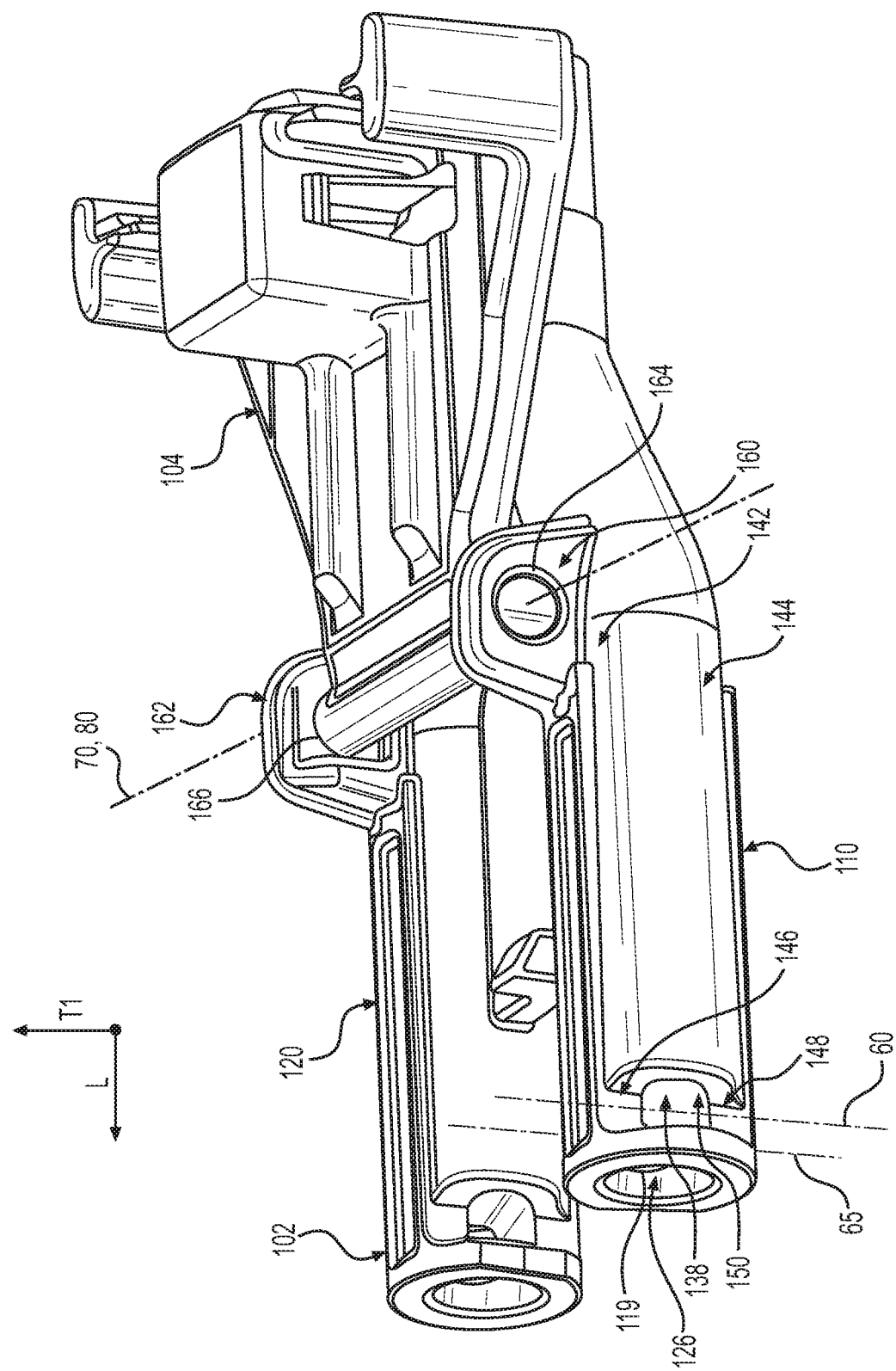
FIG. 4 illustrates a perspective view of a luer assembly in an open position, according to an aspect of this disclosure.
Figure 5:
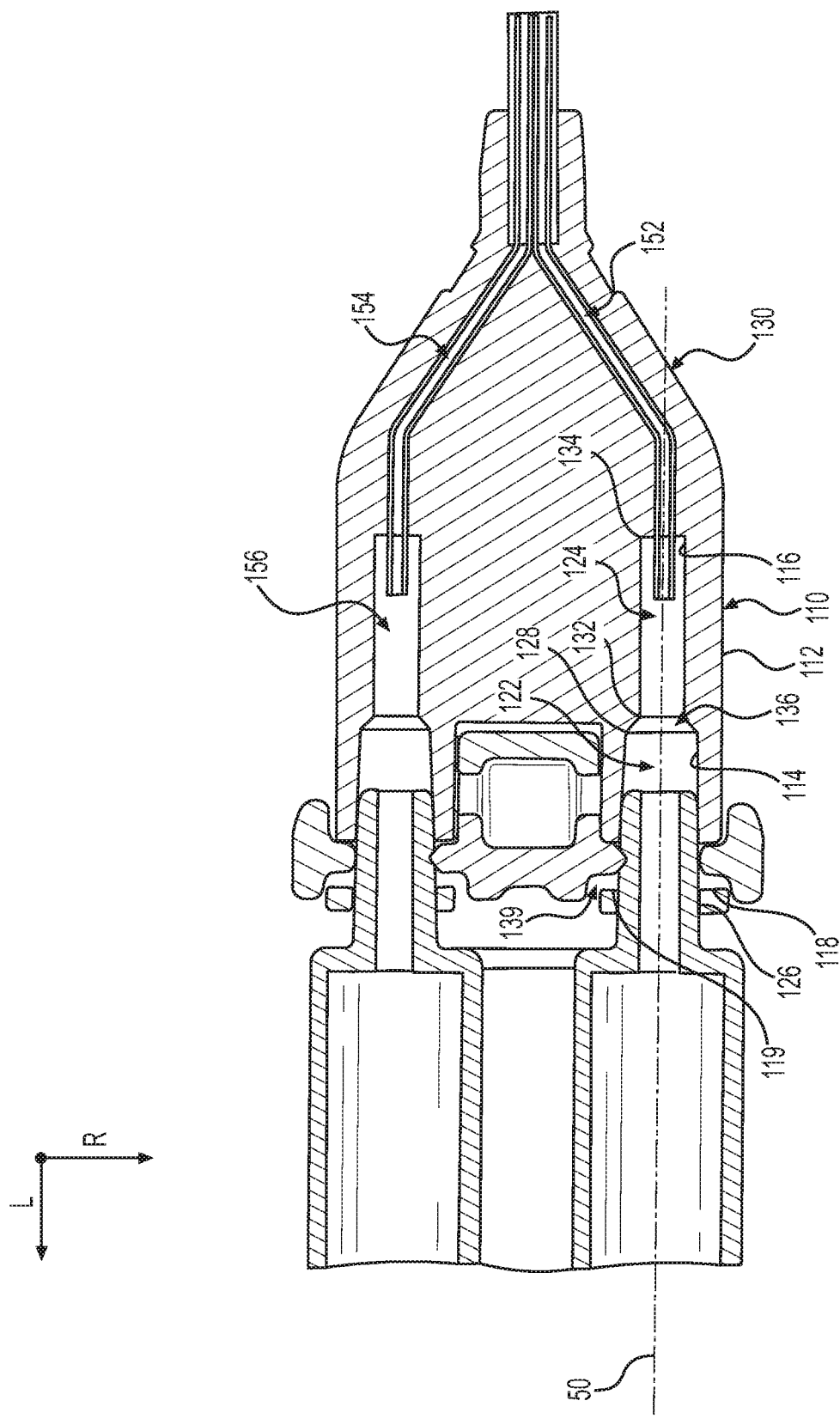
FIG. 5 illustrates a top cross-sectional view of the luer assembly taken along line 5-5 of FIG. 3, according to an aspect of this disclosure.

FIGS. 1-3 illustrate perspective views of a syringe 10 coupled to a tube 20 via a luer assembly 100, according to an aspect of this disclosure. A distal end 105 of the syringe 10 is coupled to a proximal end 101 of the luer assembly 100, and a distal end 103 of the luer assembly 100 is coupled to a proximal end 107 of the tube 20. The interconnection of the syringe 10, luer assembly 100, and tube 20 forms a fluid channel (not labeled) that extends from a proximal end 109 of the syringe 10 to a distal end 111 of the tube 20, such that a fluid may be transmitted from the syringe 10 to the tube 20 through the luer assembly 100.

The syringe 10 includes a syringe body 11, at least one channel opening 12, and at least one male luer 14. For example, two channel openings 12 and two corresponding male luers are shown in FIG. 1. The at least one channel opening 12 is located at the proximal end 109 of the syringe 20. The at least one male luer 14 is positioned at the distal end 105 of the syringe 20 and is fluidly coupled to the at least one channel opening 12 via the syringe body 11, such that fluid may flow from the at least one channel opening 12 through the syringe body 11 to the at least one male luer 14. The at least one male luer 14 may be formed, coupled, disposed or otherwise positioned on the distal end 105 of the syringe 10. The syringe 10 may be any type of syringe commonly used in the art configured to transmit a fluid.

The tube 20 may be coupled to the distal end 103 of the luer assembly 100 to form a substantially leak-free seal. The tube 20 may be coupled to the luer assembly 100 by means commonly used in the art, such as a friction fit, using an adhesive, over molding of the luer assembly 100 over the proximal end 107 of the tube 20, and/or welding. The tube 20 may include, for example, a catheter tube, an intravenous tube, a feeding tube or other flexible tube used for transferring fluids. The tube 20 may be made of a medical grade material.

Referring to FIGS. 2 through 5, the luer assembly 100 includes a hub member 102 and a latch member 104. As illustrated, the latch member 104 is rotatably coupled to the hub member 102 by a hinged connection 106. In alternative aspects, the latch member 104 may be slidably coupled to the hub member 102, or by other coupling means.

The hub member 102 includes a first hub receiving portion 110, a second hub receiving portion 120, a link portion 130, and a support portion 140. The first hub receiving portion 110 and the second hub receiving portion 120 are coupled to the link portion 130, such that the first and second hub receiving portions 110 and 120 extend from the link portion 130 in a longitudinal direction L. The longitudinal direction L extends from the distal end 103 of the luer assembly 100 to the proximal end 101 of the luer assembly 100. A proximal end of the first hub receiving portion 110 and a proximal end of the second hub receiving portion 120 may each compose a portion of the proximal end 101 of the luer assembly 100. A distal end of the link portion 130 may compose a portion of the distal end 103 of the luer assembly 100.

The support portion 140 may be coupled to the first hub receiving portion 110, the second hub receiving portion 120, the link portion 130, or combinations thereof. The support portion 140 may extend from the link portion 130 in the longitudinal direction L and be configured to provide structural support to the hub member 102. The first hub receiving portion 110, the second hub receiving portion 120, the link portion 130, and the support portion 140 may be individual components coupled together, or may be integrally formed as a single hub member 102 manufactured or otherwise formed together.

The first hub receiving portion 110 and the second hub receiving portion 120 may be coupled to the link portion 130 in a substantially similar manner. In this regard, the first and second hub receiving portions 110 and 120 may extend in substantially the same direction, for example, in the longitudinal direction L. In alternative aspects, the hub member 102 may include a single hub receiving portion, for example, either the first or the second hub receiving portions 110 and 120, or the hub member 102 may include more than the two first and second hub receiving portions 110 and 120, for example, three or more hub receiving portions. The description provided below is with respect to the first receiving portion 110, however, it will be appreciated that the description may apply to the second hub receiving portion 120 and/or any other hub receiving portion composing the hub member 102.

The first hub receiving portion 110 includes an outer hub surface 112, a first inner hub surface 114, a second inner hub surface 116, a first window surface 118, and a second window surface 119. The first inner hub surface 114 may extend circumferentially about a longitudinal axis 50, and may define a first channel 122. The first channel 122 extends from the proximal end of the first hub portion 110 towards the distal end of the first hub portion 110. The second inner hub surface 116 may extend circumferentially about the longitudinal axis 50, and may define a second channel 124. The second channel 124 extends from the first channel 122 to the distal end of the first hub portion 110. The longitudinal axis 50 may be substantially parallel to the longitudinal direction L.

The first channel 122 includes a first channel opening 126 at a proximal end of the first channel 122 and a second channel opening 128 at a distal end of the first channel 122. The first channel opening 126 may open to the outer hub surface 112. The second channel opening 128 may open to the second channel 124.

In an aspect of this disclosure, the first inner hub surface 114 may be parallel to the longitudinal axis 50, whereby the first channel opening 126 has a substantially similar diameter to the second channel opening 128. In an alternative aspect, first inner hub surface 114 may extend outwardly from the distal end of the first channel 122 to the proximal end of the first channel 122, forming a conical shape about the longitudinal axis 50. In this aspect, the first channel opening 126 may have a larger diameter than the second channel opening 128.

The second channel 124 may include a third channel opening 132 at a proximal end of the second channel 124 and a fourth channel opening 134 at a distal end of the second channel 124. The third channel opening 132 may open to the first channel 122, such that the first channel 122 is in fluid communication with the second channel 124. The fourth channel opening 134 may open to the link portion 130.

In an aspect of this disclosure, the first channel 122 may align with the second channel 124 along the longitudinal axis 50. The alignment of the first channel 122 and the second channel 124 may form a shoulder 136. The shoulder 136 may extend circumferentially about the longitudinal axis 50. In an aspect, a diameter of the second channel 124 may be less than a diameter of the first channel 122, thereby forming the shoulder 136.

In an alternative aspect, the first hub receiving portion 110 may include a single inner hub surface. For example, the single inner hub surface may include the first inner hub surface 114, such that the first channel 122 defined by the first inner hub surface 114 extends from the proximal end of the first hub portion 110 to the distal end of the first hub portion 110.

The first window surface 118 may define a first window or window channel 138. The first window 138 may extend in a radial direction R from the first inner hub surface 114 to the outer hub surface 112, such that the inner hub surface 114 is in fluid communication with the outer hub surface 112 via the first window 138. The second window surface 119 may define a second window or window channel (not visible in figures), which has substantially the same size and shape as the first window 138. The second window may oppose the first window 138 in the radial direction R and may extend from the first inner hub surface 114 to the outer hub surface 112, such that the first inner hub surface 114 is in fluid communication with the outer hub surface 112 via the second window. The radial direction R may extend radially outward from the longitudinal axis 50 and be substantially perpendicular to the longitudinal direction L. In alternative aspects, the hub member 102 may include a single window, such as first window 118, multiple windows, such as first window 118 and second window defined by window surface 119, or other windows extending from the first inner hub surface 114 to the outer hub surface 112.

The hub member 102 further includes an upper portion 142 and a lower portion 144 opposing the upper portion 142 in a transverse direction T1. The transverse direction T1 may be substantially perpendicular to the longitudinal direction L. The upper portion 142 defines an upper groove 146, and the lower portion 144 defines a lower groove 148. The upper groove 146, the lower groove 148, and the window 138 may be aligned in the transverse direction T1 so as to form a first blade channel 150. The first blade channel 150 may extend at least partially through the hub member 102 in the transverse direction T1 along a first transverse axis 60, which is substantially parallel to the transverse direction T1. Similarly, a second blade channel (not visible in figures) may be formed on a side of the first hub receiving portion 110 opposing the first blade channel 150 in the radial direction R. The second blade channel may extend along a second transverse axis 65 and have substantially the same size and shape as the first blade channel 150. The second transverse axis 65 may extend substantially parallel to the first transverse axis 60.

The hub member 102 may further include a first hinged connection 160 and a second hinged connection 162. The first and second hinged connections 160 and 162 may be located on the upper portion 142 of the hub member 102, and may extend from the hub member 102 in the transverse direction T1. The first hinged connection 160 may define a first hinge opening 164, and the second hinged connection 162 may define a second hinge opening 166. The first and second hinge openings 164 and 166 may extend through the respective first and second hinged connections 160 and 162 along a hinge lateral axis 70, which extends from the first hinged connection 160 to the second hinged connection 162.

The link portion 130 may define a first link channel 152 and a second link channel 154. Both the first and second link channels 152 and 154 extend through the link portion 130 from a proximal end to a distal end of the link portion 130. A proximal end of the first link channel 152 is configured to open to the second channel 124. Similarly, a proximal end of the second link channel 154 opens to a third channel 156 defined within the second hub portion 112. A distal end of both the first link channel 152 and the second link channel 154 open to the distal end of the link portion 130. Alternatively, the respective distal ends of the first link channel 152 and the second link channel 154 may open to one another, thereby forming a third link channel (not shown) extending from the distal ends of the first link channel 152 and the second link channel 154 to the distal end of the link portion 130.

Figure 6:
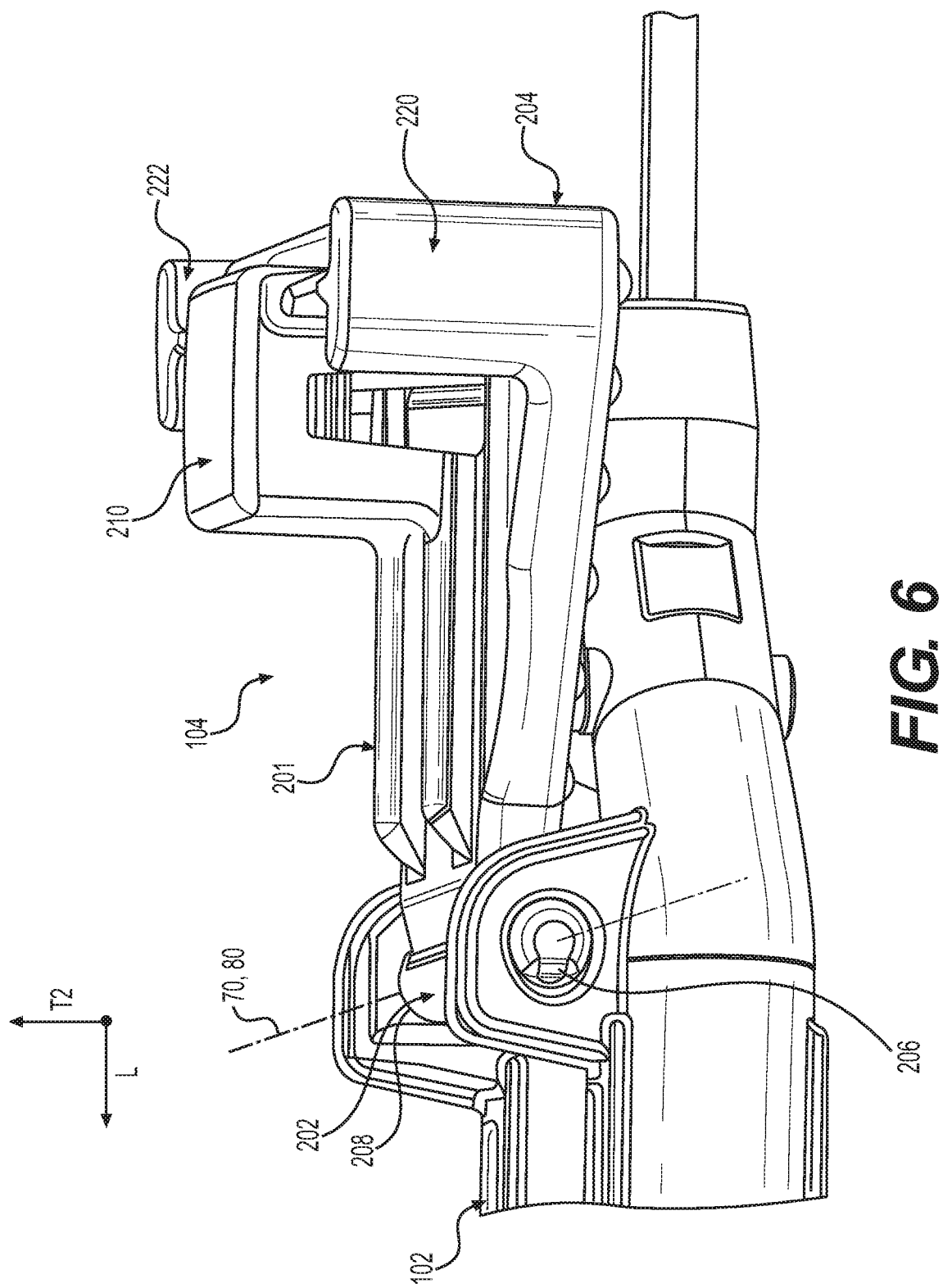
FIG. 6 illustrates a side view of a distal end of a luer assembly in an open position, according to an aspect of this disclosure.
Figure 7:
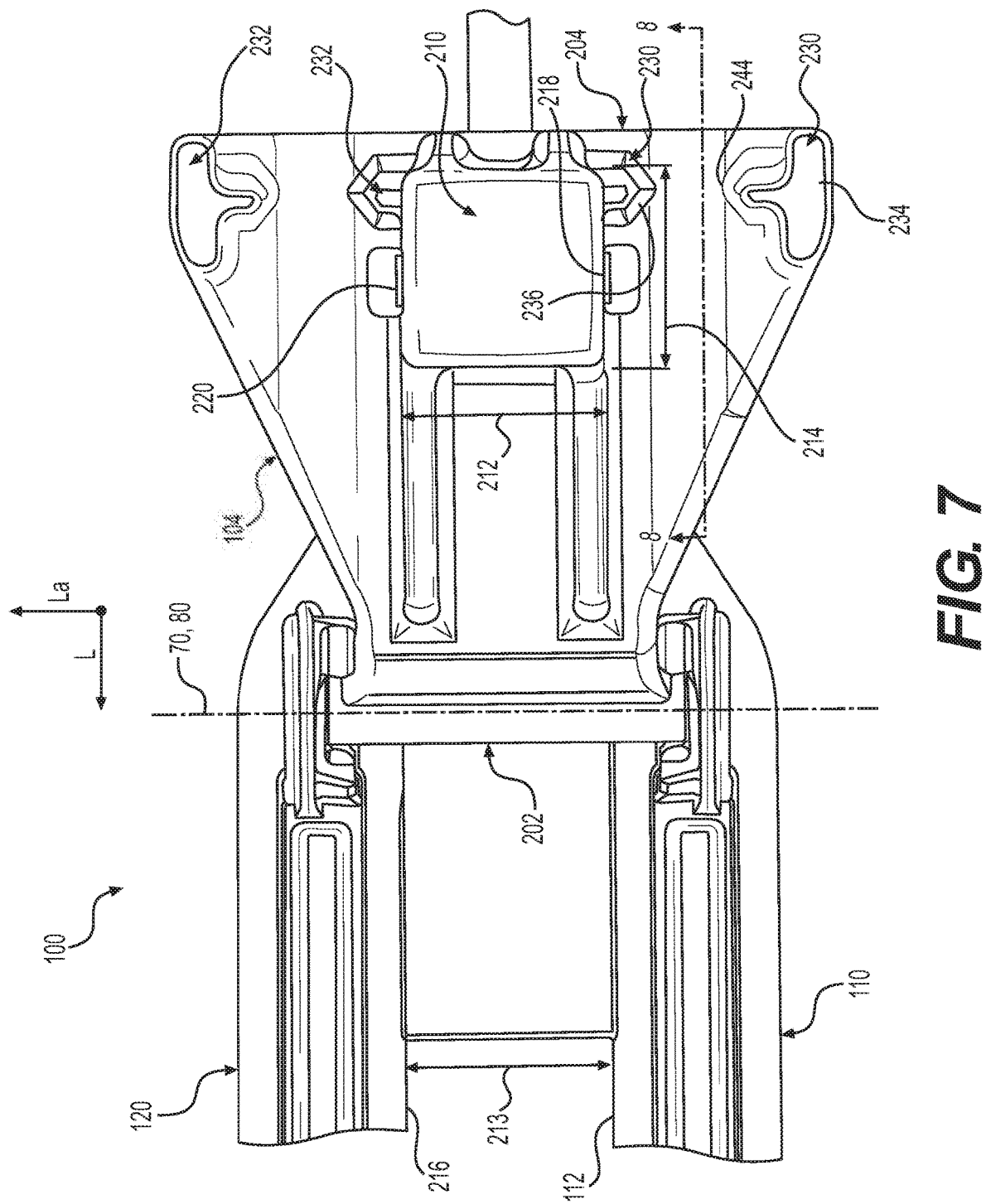
FIG. 7 illustrates a top view of a distal end of a luer assembly in an open position, according to an aspect of this disclosure.

FIGS. 6 and 7 illustrate the latch member 104 coupled to the hub member 102 from a perspective view and a top view, respectively. The latch member 104 includes a first latch end 202, a second latch end 204, and a latch body 201 that extends from the first latch end 202 to the second latch end 204. The first latch end 202 includes a first hinge pin 206 and a second hinge pin 208 opposing the first hinge pin 206 along a latch lateral axis 80. Each of the first and second hinge pins 206 and 208 extend from the latch body 201 along the latch lateral axis 80. The first hinge pin 206, the second hinge pin 208, the first hinged connection 160, and the second hinged connection 162 may compose the hinged connection 106 between the latch member 104 and the hub member 102.

The second latch end 204 of the latch member 104 includes a lock portion 210, a first blade member 230, and a second blade member 232. The lock portion 210 extends from the latch body 201 in a latch transverse direction T2. The lock portion 210 may have a rectangular cuboid or cubic shape, with a width dimension 212 and a length dimension 214. The width dimension 212 may extend in a lateral direction La, and the length dimension 214 may extend in the longitudinal direction L. The lateral direction La may be substantially perpendicular to the longitudinal direction L.

The magnitude of the width dimension 212 may depend on a distance 213 between the outer hub surface 112 of the first hub receiving portion 110 and an outer surface 216 of the second hub receiving portion 120. For example, the size of the width dimension 212 may be such that the lock portion 210 may fit between the first hub receiving portion 110 and the second hub receiving portion 120 in the lateral direction La.

The lock portion 210 may include a first lock element 218 and a second lock element 220. The first lock element 218 and the second lock element 220 may be positioned on sides of the lock portion 210 opposing each other in the lateral direction La. The second lock element 220 extends out from the lock portion 210 in the lateral direction La, and the first lock element 218 extends from the lock portion 210 in a direction opposing the lateral direction La.

The first blade member 230 and a second blade member 232 may extend from the latch body 201 in the latch transverse direction T2. Each of the first and second blade members 230 and 232 may extend from the latch body 201 in a substantially similar manner, such that they form mirror images of each other when viewed from the longitudinal direction L. In alternative aspects, the latch member 104 may include a single blade portion, for example, either the first or the second blade members 230 and 232, or the latch member 104 may include more than the two first and blade members 230 and 232, for example, three or more blade members. The number of blade members 230 and 232 may be related to the number of hub receiving portions 110 and 112, such that the number of blade members 230 and 232 is equivalent to the number of hub receiving portions 110 and 112. The description provided below is with respect to the first blade member 230; however, it will be appreciated that the description may apply to the second blade member 232 and/or any other blade portion composing the latch member 104.

The first blade member 230 includes a first blade body 234 and a second blade body 236 opposing the first blade body 234 in the lateral direction La. The first and second blade bodies 234 and 236 may extend to a substantially similar distance from the latch body 201 in the latch transverse direction T2.

Figure 8:
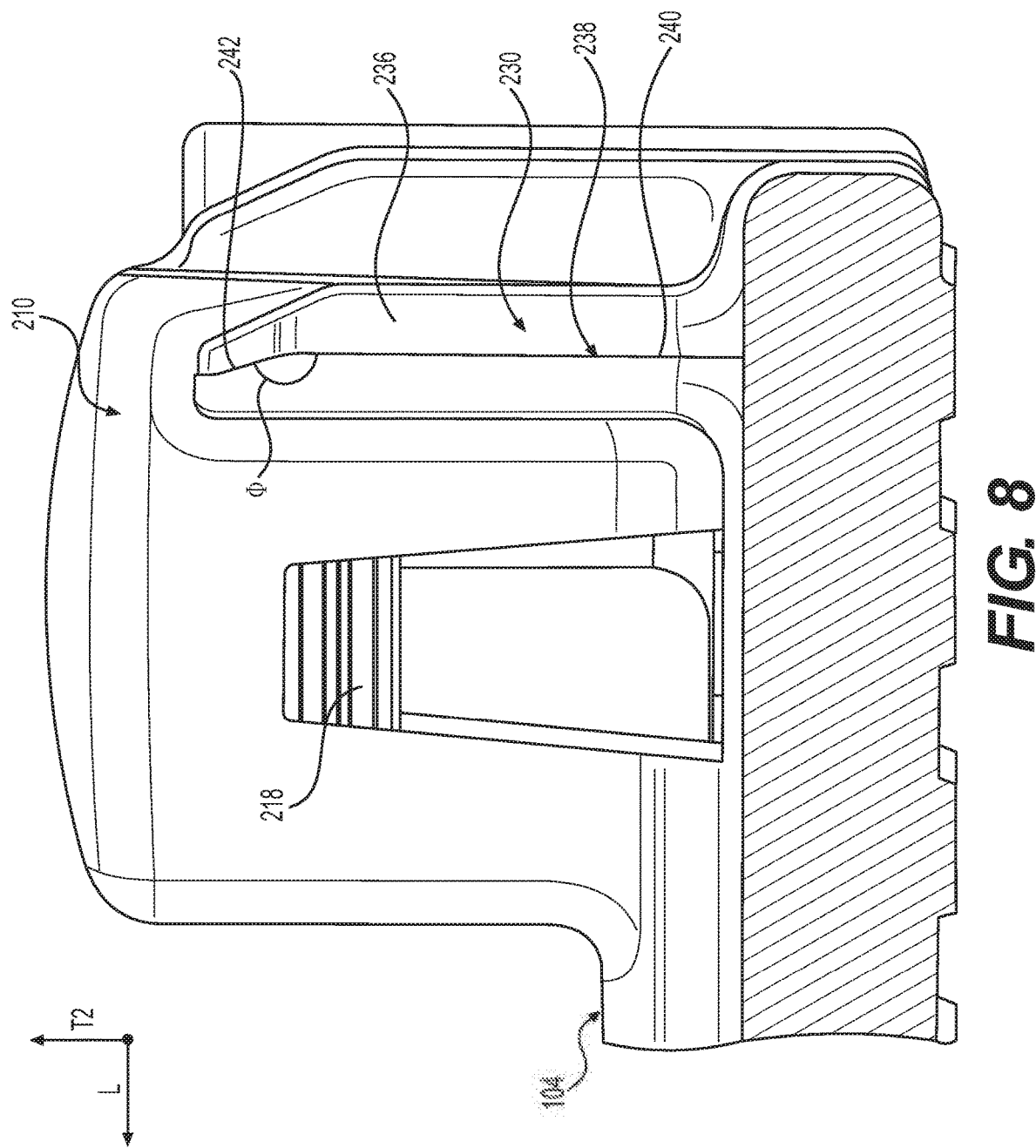
FIG. 8 illustrates a side cross-sectional view of the luer assembly taken along line 8-8 of FIG. 7, according to an aspect of this disclosure.

FIG. 8 illustrates a cross-sectional side view of the second latch end 204 of the latch member 104 as viewed from the lateral direction La taken along line 8-8 of FIG. 7. The second blade body 236 includes a first blade 238 that extends from a bottommost end of the second blade body 236 to an uppermost end of the second blade body 236. The first blade 238 includes a first blade portion 240 and a second blade portion 242. The first blade portion 240 extends from the latch body 201 to the second blade portion 242, and the second blade portion 242 extends from the first blade portion 240 towards the uppermost end of the second blade body 236. The second blade portion 242 may be linear or curvilinear in shape. The first blade portion 240 may be angularly offset from the second blade portion 242 by an offset angle Φ. For example, if the first blade portion 240 is aligned with the latch transverse direction T2, the second blade portion 242 extends at least partially in both the longitudinal direction L and the latch transverse direction T2 forming the offset angle Φ between the first and second blade portions 240 and 242. The offset angle Φ may be any angle between 0 and 180 degrees, inclusive.

The first blade body 234 includes a second blade 244 that extends from a bottommost end of the first blade body 234 to an uppermost end of the first blade body 234. The second blade 244 faces the first blade 238 of the second blade body 236 in the lateral direction La. The first blade body 234 may be configured substantially similarly to the second blade body portion 236. For example, the first blade 238 a may be a mirror image of the second blade 244 when viewed from the longitudinal direction L. The second blade 244 may include a first blade portion (not visible in figures) corresponding to the first blade portion 240 of the first blade 238, and a second blade portion (not visible in figures) corresponding to the second blade portion 242 of the first blade 238.

The second end 202 of the latch member 104 may be rotably coupled to the hub member 102 by positioning the first hinge pin 206 and the second hinge pin 208 within the first hinge opening 164 and the second hinge opening 166, respectively. The connection between the first and second hinge pins 206 and 208 with the first and second hinge openings 164 and 166 may define, for example, a swivel hinge. When the first and second hinge pins 206 and 208 are positioned within the first and second hinge openings 164 and 166, the hinge lateral axis 70 may align with the latch lateral axis 80. The first and second hinge pins 206 and 208 secure the latch member 104 to the hub member 102 and allow the latch member 104 to rotate about the hinge lateral axis 70 relative to the hub member 102. The latch member 104 may rotate about the hinge lateral axis 70 from an open position (as illustrated in FIG. 2) to a closed or locked position (as illustrated in FIG. 3).

The syringe 10 is coupled to the luer assembly 100 by sliding the at least one male slip luer 14 at the distal end 105 of the syringe 10 into the first hub receiving portion 110 and/or the second hub receiving portion 120. The at least one male slip luer 14 may be slid into and retained in either of the first and second hub receiving portions 110 and 120 in a substantially similar manner. The description provided below is with respect to the first hub receiving portion 110, however, it will be appreciated that the description may apply to the second hub receiving portion 120 and/or any other hub receiving portion composing the hub member 102.

The at least one male slip luer 14 may have an outer surface with dimensions substantially similar to the shape defined by the first inner hub surface 114 of the first hub receiving portion 110. For example, if the first inner hub surface 114 forms a conical shape, the at least one male slip luer 14 may have a substantially similar conical shape. In this regard, when the at least one male slip luer 14 is positioned within the first channel 122 of the first hub receiving portion 110, at least a portion of the outer surface of the at least one male slip luer 14 is in contact with the inner hub surface 114. The contact between the outer surface of the at least one male slip luer 14 and the inner hub surface 114 may at least partially secure the at least one male slip luer 14 to the first hub receiving portion 110.

The at least one male slip luer 14 may be slid into the first channel 122 of the first hub receiving portion 110 so that a distal end of the at least one male slip luer 14 contacts the shoulder 136. The shoulder 136 may prevent the at least one male slip luer 14 from further extending into the first hub receiving portion 110. Alternatively, the at least one male slip luer 14 may extend partially into the first channel 122 when slid into the first hub receiving portion 110, such that the distal end of the at least one male slip luer 14 is positioned between the proximal end and the distal end of the first channel 122. The contact between the outer surface of the at least one male slip luer 14 and the inner hub surface 114 may prevent the at least one male slip luer 14 from contacting the shoulder 136.

The latch member 104 is configured to lock and/or secure the syringe 10 within the hub member 102. When the at least one male slip luer 14 is positioned with the first channel 122, at least a portion of the at least one male slip luer 14 may project into the first blade channel 150 and the second blade channel 151. The latch member 104 may then be rotated about the hinge lateral axis 70 from the open position to the locked position, so that the first blade body 234 and second blade body 236 of the first blade member 230 come into alignment with the first blade channel 150 and the second blade channel 151, respectively. When the latch member 104 is in the closed position, the first blade 238 and the second blade 244 are spaced apart from each other such that each of the blades 238 and 244 contact the outer surface of the at least one male slip luer 14, substantially preventing the syringe 10 from sliding in and out of the first channel 122.

The rotation of the latch member 104 may be described by defining various positions of the latch member 104 relative to the hub member 102. For example, the latch member 104 may include a first position, a second position, and a third position. In the first position, the latch member 104 may be in the open position, such that neither the first blade 238 nor the second blade 244 is positioned within either of the first and second blade channels 150 and 151. In the second position, the latch member 104 may be rotated about the hinge lateral axis 70 to a position such that the first blade member 230 is initially entering the first and second blade channels 150 and 151 from the upper portion 142 of the hub member 102. In the third position, the latch member 104 may be rotated about the hinge lateral axis 70 to the closed position, such that both the first blade 238 and the second blade 244 are positioned within the first blade channel 150 and the second blade channel, respectively.

Figure 9A:
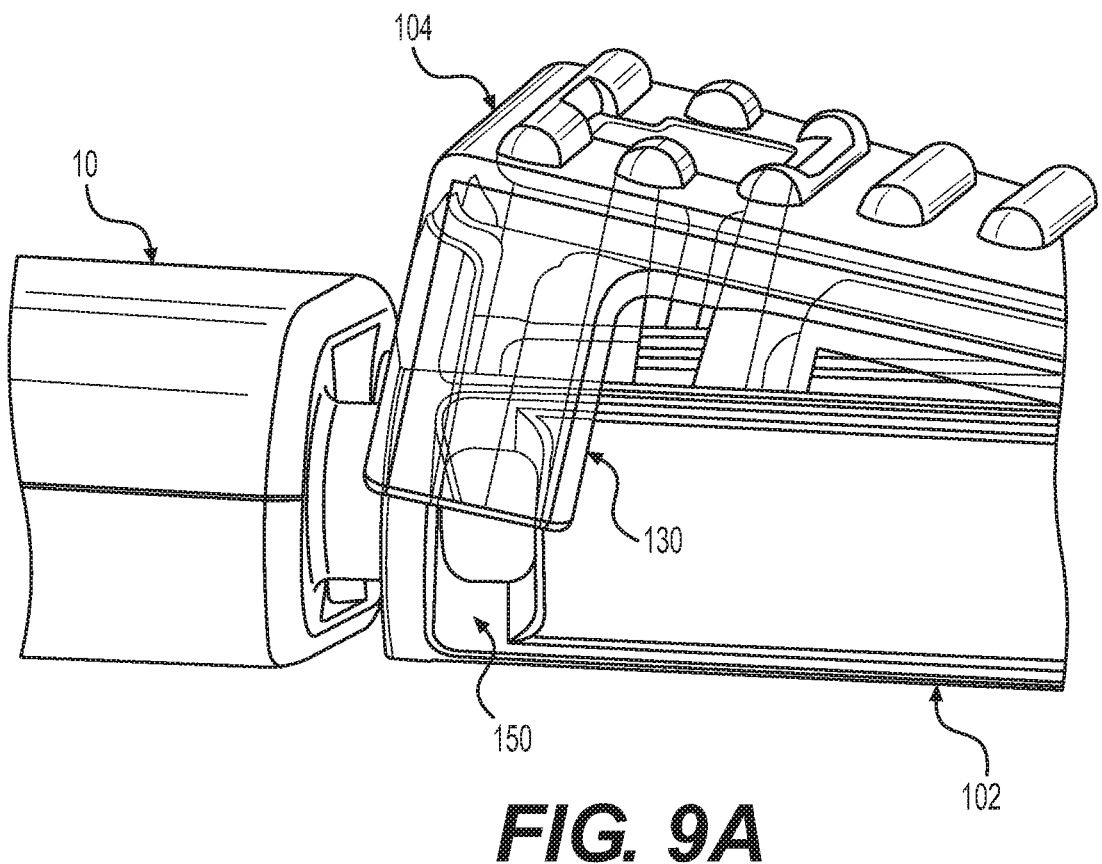
FIG. 9A illustrates a side view of a syringe positioned within a luer assembly, the luer assembly in a first position, according to an aspect of this disclosure.
Figure 9B:
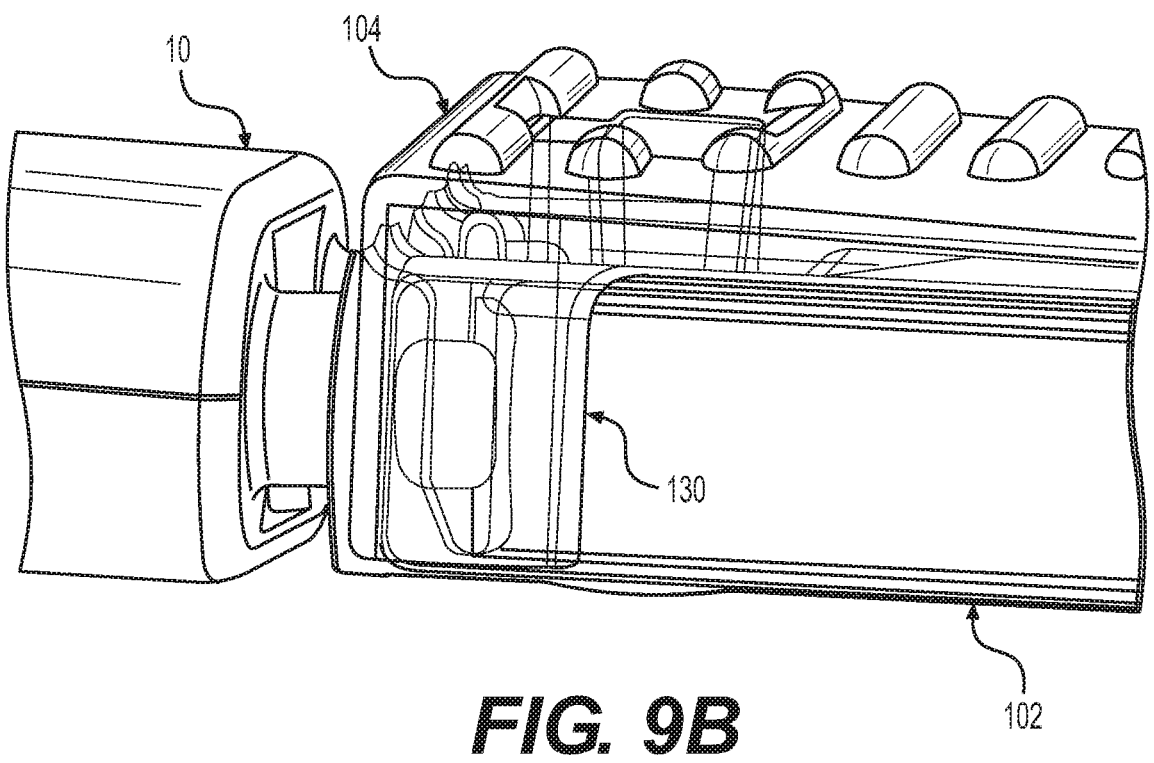
FIG. 9B illustrates a side view of a syringe positioned within a luer assembly, the luer assembly in a second position, according to an aspect of this disclosure.

FIGS. 9A and 9B illustrate side views of the syringe 10 positioned within the luer assembly 100. FIG. 9A shows the latch member 104 in the second position, and FIG. 9B shows the latch member 104 in the third position. In the second position, the second blade portion 242 of the first blade 238 may align with the second transverse axis 65 such that the second blade portion 242 is parallel to the second transverse axis 65. The second blade portion (not visible in figures) of the second blade 244 may align with the first transverse axis 60, such that the second blade portion of the second blade 244 is parallel to the first transverse axis 60. In this regard, the spacing of the first blade member 230 and the second blade member from the first hinge pin 206 and second hinge pin 208 along the latch body 201 may depend upon the offset angle Φ between the first and second blade portions 240 and 242. Alternatively, the offset angle Φ may depend upon the spacing of the first and second blade member 230 and 232 from the first and second hinge pins 206 and 206 along the latch body 201.

In the third position, the first blade member 230 is at least partially within the first and second blade channels 150 and 151. In an aspect, the first blade member 230 may extend fully through the first and second blade channels 150 and 151. In the third position, the first blade portion 240 of the first blade 238 may align with the second transverse axis 65 such that the first blade portion 240 is parallel to the second transverse axis 65. The first blade portion (not visible in figures) of the second blade 244 may align with the first transverse axis 60, such that the first blade portion of the second blade 244 is parallel to the first transverse axis 60.

As the latch member 104 is rotated from the second position to the third position, the rotational motion of the first and second blades 238 and 244 relative to the hub member 102 provide a force on the at least one male luer 14 pulling the at least one male luer 14 towards the distal end of the first channel 122. The force applied to the at least one male luer 14 creates a tight seal between the at least one male luer 14 and the inner hub surface 114 of the first hub receiving portion 110. The luer assembly 100 may be a slip luer assembly, or alternatively, the luer assembly 100 may also include lock luer assemblies or other types of luer connectors.

After the latch member 104 has been rotated to the third position, the latch member 104 may be locked to the hub member 102. The first lock element 218 and a second lock element 220 may engage with the outer surface 216 of the second hub receiving portion 120 and the outer hub surface 112 of the first hub receiving portion 110, respectively. The engagement between the first and second lock elements 218 and 220 with the first and second hub receiving portions 110 and 120 may provide a feedback, such as an auditory feedback or a tactile feedback, which indicates that the latch member 104 is in the third position. The first and second lock elements 218 and 220 may be, for example, snap clips, snap locks, or other fasteners that can substantially prevent movement of the latch member 104 relative to the hub member 102.

To operate the luer assembly 100, an operator, such as a surgeon, may insert the syringe 10 into the luer assembly 100 such that a first at least one male luer 14 and a second at least one male luer 14 are positioned within the first hub receiving portion 110 and the second hub receiving portion 120, respectively. The operator may then actuate the latch member 104 to rotate from the first, open position, to the third, closed position, locking the syringe 10 to the luer assembly 100. The proximal end 107 of the tube 20 may be coupled to the distal end 103 of the luer assembly 100. The operator may then transfer fluid from the syringe 10 to the tube 20 through the luer assembly 100.

After the fluid transfer through the luer assembly 100 is complete, the operator may release the first and second lock elements 218 and 220 and actuate the latch from the third, closed position, to the first, open position. The syringe 10 may then be removed from the luer assembly 100 by sliding the first and second at least one male luer 14 out of the first hub receiving portion 110 and the second hub receiving portion 120, respectively.

It will be appreciated that the foregoing description provides examples of the disclosed system and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed is:

1. An assembly, comprising:
   a hub member having a hub receiving portion, the hub receiving portion comprising:
      an outer hub surface,
      an inner hub surface defining a channel, the channel extending at least partially through the hub member in a longitudinal direction of the hub member, the channel configured to receive a male luer at least partially within, the channel being configured to receive the male luer as the male luer is slid into the channel in the longitudinal direction, and
      a window surface defining a window extending from the outer hub surface to the inner hub surface; and
   a latch member coupled to the hub member, the latch member including at least one blade,
   wherein the latch member is configured to be actuated between a first position and a second position, wherein in the first position, the at least one blade is not positioned within the window of the hub member, and wherein in the second position, the at least one blade is positioned at least partially within the window of the hub member, and
   wherein the at least one blade of the latch member is aligned with the hub member such that as the latch member is actuated from the first position to the second position and the male luer is positioned within the channel, the at least one blade enters the window of the hub member and contacts an outer surface of the male luer to prevent the male luer from sliding into the channel in the longitudinal direction and to prevent the male luer from sliding out of the channel in the longitudinal direction.

2. The assembly of claim 1, wherein the channel is a luer channel, the luer channel being adapted for receiving the male luer within, wherein when the male luer is positioned within the luer channel and the latch member is in the second position, the male luer is substantially restricted from sliding within the luer channel, and wherein when the male luer is positioned within the luer channel and the latch member is in the first position, the male luer is freely slidable within the luer channel.

3. The assembly of claim 2, wherein when the latch member is in the second position and the male luer is within the luer channel, the at least one blade is engaged with the male luer.

4. The assembly of claim 2, wherein the channel extends in the longitudinal direction, and wherein the window extends from the outer hub surface to the inner hub surface in a radial direction, the radial direction being substantially perpendicular to the longitudinal direction.

5. The assembly of claim 4, wherein the hub member further includes an upper portion, a lower portion opposing the upper portion in a transverse direction, an upper groove in the upper portion, and a lower groove in the lower portion, wherein the upper groove, the lower groove, and the window surface form a blade channel that extends in the transverse direction at least partially through the hub member, and wherein the transverse direction is substantially perpendicular to the longitudinal direction.

6. The assembly of claim 5, wherein the at least one blade includes a first blade portion and a second blade portion, wherein the first blade portion is angularly offset from the second blade portion.

7. The assembly of claim 6, wherein when the latch member is actuated from the first position to the second position, the first blade portion is configured to be substantially parallel to the blade channel when the first blade portion initially enters the blade channel.

8. The assembly of claim 7, wherein when the latch member is in the second position, the second blade portion is configured to be substantially parallel to the blade channel.

9. The assembly of claim 8, wherein when the latch member is actuated from the first position to the second position, rotation of the latch member provides a force that pulls the male luer further into the channel of the hub member creating a tight seal.

10. The assembly of claim 4, wherein the window surface is a first window surface and the window is a first window, wherein the hub member further includes a second window surface defining a second window extending from the outer hub surface to the inner hub surface, wherein in the second position, a first blade of the at least one blade is positioned at least partially within the first window of the hub member and a second blade of the at least one blade is positioned at least partially within the second window of the hub member, and wherein in the first position, the first and second blades are not positioned within the first window and the second window of the hub member, respectively.

11. The assembly of claim 10, wherein the first window and the second window of the hub member oppose each other in the radial direction.

12. The assembly of claim 1, further comprising:
a second hub member having a second hub receiving portion, the second hub receiving portion comprising:
a second outer hub surface,
a second inner hub surface defining a second channel, the second channel extending at least partially through the second hub member, and
a second window surface defining a second window extending from the second outer hub surface to the second inner hub surface,
wherein the hub member and the window are a first hub member and a first window, respectively, wherein in the first position, a first blade of the at least one blade is not positioned within the first window of the first hub member and a second blade of the at least one blade is not positioned within the second window of the second hub member, and wherein in the second position, the first and second blades are positioned at least partially within the first window and the second window, respectively.

13. The assembly of claim 1, wherein the latch member is rotatably coupled to the hub member.

14. The assembly of claim 13, wherein the hub member further includes a swivel hinge, and wherein the latch member further includes a first end and a second end opposing the first end, wherein the at least one blade is positioned toward the second end, and wherein the first end is rotatably coupled to the swivel hinge.

* * * * *